United States Patent [19]

Warner

[11] Patent Number: 5,008,107
[45] Date of Patent: Apr. 16, 1991

[54] ATTRACTANT COMPOSITION FOR SYNANTHROPIC FLIES

[75] Inventor: William B. Warner, Phoenix, Ariz.

[73] Assignee: Farnam Companies, Inc., Phoenix, Ariz.

[21] Appl. No.: 534,292

[22] Filed: Jun. 6, 1990

Related U.S. Application Data

[63] Continuation-in-part of Ser. No. 472,708, Jan. 31, 1990, abandoned, which is a continuation-in-part of Ser. No. 197,696, May 23, 1988, abandoned, which is a continuation of Ser. No. 889,217, Jul. 25, 1986, abandoned.

[51] Int. Cl.$^5$ .............................................. A01N 25/00
[52] U.S. Cl. ...................................................... 424/84
[58] Field of Search ........................................... 424/84

[56] References Cited

U.S. PATENT DOCUMENTS

| 3,162,575 | 12/1964 | Lang | 424/84 |
| 3,576,834 | 4/1971 | Buchanan | 560/153 |
| 3,846,557 | 11/1974 | Mulla et al. | 426/1 |
| 3,996,349 | 12/1976 | Mulla et al. | 424/84 |
| 4,122,165 | 10/1978 | Kinzer et al. | 424/84 |
| 4,205,066 | 5/1980 | Hennart et al. | 424/84 |

OTHER PUBLICATIONS

The Merck Index 10th Ed. #212 (1983).

*Primary Examiner*—Allen J. Robinson
*Attorney, Agent, or Firm*—Joseph H. Roediger

[57] ABSTRACT

Novel attractant composition for use with synanthropic flies which includes indole and skatole, a pheromone, trimethylamine hydrochloride, and a suitable carrier.

10 Claims, No Drawings

ATTRACTANT COMPOSITION FOR SYNANTHROPIC FLIES

This application is a continuation-in-part of application Ser. No. 07/472,708, filed Jan. 31, 1990, now abandoned, which is a continuation-in-part of application Ser. No. 07/197,696, filed May 23, 1988, now abandoned which is a continuation of application Ser. No. 06/889,217, filed July 25, 1986, now abandoned.

BACKGROUND OF THE INVENTION

This invention relates to attractant compositions for synanthropic flies. Throughout history, synanthropic flies have distinguished themselves as persistent pests and health threats to both man and animals. Studies have been made documenting flies as carriers of disease. As a result, substantial time and effort has been expended to develop pesticides and insecticides which can be broadcast throughout entire areas either in the form of sprays or as solids in order to shorten the life of these insects. Recent studies have shown that the widespread use of insecticides in an indiscriminate manner has far greater ramifications than originally thought when the impact on man and his environment is examined. Consequently, there has been increasing interest generated in localized trapping of pests by the use of attractants which draw them to a central location containing the specific agents for eliminating them.

Synanthropic flies are prolific breeders and experiments have been conducted directed to the control of the breeding process to reduce the fly population. Also, studies directed to the identification and synthesis of a sex attractant pheromone of the house fly, *Musca domestica*, were conducted successfully several years ago and resulted in the isolation of the pheromone cis-9-tricosene. This sex pheromone has received wide acceptance as an attractant for house flies. The synthesis of such pheromones is relatively expensive, rendering their widespread application costly. As a result, cis-9-tricosene is normally used in combination with low-cost carriers, thereby reducing the overall costs.

Furthermore, because flies are known to breed in environments promoting fermentation and microbial degradation, some attempts have been made to create fly attractants that have centered about the use of putrified or fermented materials (U.S. Pat. No. 3,846,557) or chemical isolates thereof (U.S. Pat. No. 3,996,349) to attract flies to a central location. The compounds indole and skatole are known as feeding attractants for flies and have been used in combination with nitrogenous materials such as trimethylamine and ammonia (U.S. Pat. No. 3,996,349). These compositions can be prepared in an aqueous mixture which is used as a liquid to attract flies, or can be employed with solid carriers such as sugar, clay or other inert porous materials.

While pheromones used as sex attractants and nitrogenous matter used as feeding attractants have been developed and used in connection with both liquid and solid mixtures, long-term fly control should place greater emphasis on the attraction of the female fly. The common house fly is a polygamous creature and a proportionately small number of male flies are all that is needed to fertilize a larger female population. Thus, attracting a male fly to a trap or insecticide has an immediate effect on the existing fly population, but essentially no impact on the size of the succeeding fly generation. It is common place for a female house fly to have the reproductive capacity to produce a thousand or more offspring. The killing of a female fly removes her remaining fecundity from the next generation. Thus, any control measure that operates to remove proportionately more females than males is vastly superior in terms of its impact on the next fly generation.

Accordingly, it is an object of the present invention to provide an attractant for synanthropic flies which utilizes a number of constituents which might each serve to some degree as an attractant, but interact in a manner to provide greater than expected efficacy. A further important feature of the invention is the provision of a fly attractant exhibiting a greater attractive effect upon the female fly than the male fly. Also, the invention provides an attractant having the ability to be marketed in a concentrated form, a dry diluted form, or in a liquid form. Further, the present novel attractant utilizes a plurality of individual attractants interacting to exhibit an enhanced attractive effect for reducing the cost per attracted fly.

SUMMARY OF THE INVENTION

This invention relates to an attractant for synanthropic flies which comprises at least three attractant constituents; indole and skatole, trimethylamine hydrochloride, and cis-9-tricosene, which interact in a synergistic manner to provide a highly efficacious agent for attracting synanthropic flies to a particular location, such as a trap or a toxicant bait. A suitable carrier which also possesses attractant qualities for flies is disclosed.

The first attractant in the present composition is selected from the group of indole and skatole individually known to be feeding attractants for synanthropic flies. Indole and skatole have been found to repel flies temporarily at concentrations is excess of 0.2% by weight when utilized without other active ingredients, and to decrease attraction to multicomponent systems at those concentrations. In the present inventions, the concentration of indole and skatole is maintained within the range of 0.001 to 0.1% by weight.

To this feeding attractant is added trimethylamine hydrochloride, a hydroscopic salt with no appeal to the olfactory sense of the fly, but which provides a source of trimethylamine gas in the presence of water or humidity. This gas, when liberated from the composition, does stimulate a favorable olfactory response in the fly. The compositional range of this salt is determined in part by the carrier composition.

The third attractant constituent is a pheromone of synanthropic flies which is produced from the female fly and can act as both an aggregative and sex attractant for the fly. One such pheromone is cis-9-tricosene and is presently utilized in combination with insecticide compositions for broadcast applications and as an attractant for use with fly traps. The pheromone attractant is found to unexplainedly compliment the action of the combination of the first feeding attractant and the liberated gas, appealing to the olfactory sense of the fly.

The carrier to which these three constituents are added may include ethyl alcohol which is also present in the composition to provide a solvent for indole or skatole, and possesses some attractant characteristics for synanthropic flies as well. In addition, the carrier can include water, for example 5% by weight of the combination, in order to promote the liberation of the gaseous attractant.

The use of alcohol as a solvent for the indole and skatole feeding attractants is preferred since it facilitates the manufacture of the composition and, in the case of a solvent containing ethyl alcohol, adds to the attractancy of the composition. Furthermore, the alcohol solvent is compatible with suitable carriers which frequently contain ethyl alcohol. In the use of other solvents for the indole and skatole, the solvent is normally flashed off after a mixture of materials is prepared. The solvents for indole and skatole found useful in this mode of preparation include acetone, 1,1,1 trichloroethane and methylene chloride. The solvent selected should have a low boiling point and high vaporization rate to facilitate its evaporation from the mixture.

The attractancy of the present invention has been found to provide a surprising increase not only in efficacy when contrasted with the performance of commercially available attractant compositions, but also in the ability to attract more female then male flies. The following examples are provided to illustrate this effect with different embodiments of the present invention and are not intended as a limitation of the scope thereof. All percentages are by weight:

EXAMPLE I

Formulation A below was the commercially available Improved Golden Malrin Fly Bait (Zoecon Corporation, Dallas, Tex.). Formulations B and C below were prepared by dissolving the toxicant methomyl, s-methyl-n((methyl carbamoyl) oxy-thioacetimidate (U.S. Pat. No. 3,576,834), and cis-9-tricosene (C only) in acetone and blending with powdered sugar until thoroughly homogenized. After the solvent had evaporated from this mixture, the mixture was thoroughly blended with a slurry of pulverized trimethylamine hydrochloride, ethyl alcohol and indole, and then compressed into granules similar in size to those of formulation A.

| FORMULATION | | PERCENT |
|---|---|---|
| A. | methomyl | 1.000 |
| | cis-9-tricosene | 0.025 |
| B. | methomyl | 1.000 |
| | indole | 0.010 |
| | trimethylamine-HCl | 0.500 |
| | ethyl alcohol | 0.500 |
| C. | methomyl | 1.000 |
| | cis-9-tricosene | 0.025 |
| | indole | 0.010 |
| | trimethylamine-HCl | 0.500 |
| | ethyl alcohol | 0.500 |

Five replicate pairs, each consisting of two 12 inch cardboard bait trays set on the ground four feet apart, were set up at a public riding stable and baited one tray per pair with 10 grams of formulation A and one with 10 grams of formulation C at 0730 hours. Dead flies in the trays were counted at 45 minutes and 7 hours post baiting. Two days subsequently the same test was conducted using one formulation A and one formulation B tray per replicate. The results are given in Table I. For convenience, the mean fly counts are expressed as ratios.

TABLE I

| FORMULATION | MEAN FLY COUNT (RATIO) | |
|---|---|---|
| | 45 min | 7 hour |
| A | 1.00 | 1.00 |
| B | 0.07 | 0.05 |
| C | 8.74 | 7.06 |

The 141 fold increase in counts achieved by the addition of cis-9-tricosene to formulation B (i.e., formulation C) and the seven fold increase in counts over A achieved by the present invention, formulation C, clearly demonstrates a synergism between the individual attractants of the present invention which results in a great improvement in efficacy over prior art compositions that is unexpected and could not have been predicted.

EXAMPLE II

Formulation D was prepared as a two-phase liquid compound, the phases being mixed prior to application. The first phase consisten of bomyl (dimethyl-3-hydroxy glutaconate dimethyl phosphate) 0.5%; propoxur (2-(1-methylethoxy) phenyl methyl carbamate) 0.5%; muscalure (at 50% cis-9-tricosene) 0.1%; 1.1.1-trichloroethane 8.9%. The second phase consisted of indole 0.01%, trimethylamine hydrochloride 0.5%, ethyl alcohol (as B.A.T.F. formula S.D.A.-3C, 190 degrees) 21%, xanthan gum 0.25%, powdered sugar 25%, and water 43.19%. The results of a five replicate test of this embodiment of the present invention in accordance with, and at the same site as in Example I, are shown in Table II.

TABLE II

| FORMULATION | MEAN FLY COUNT (RATIO) | | |
|---|---|---|---|
| | 45 min | 8.5 hr | 24 hr |
| A | 1.00 | 1.00 | 1.00 |
| D | 4.56 | 3.57 | 4.86 |

EXAMPLE III

Formulation E was a liquid concentrate prepared in accordance with the present invention and diluted one ounce per one-half gallon water during baiting. Formulation E comprised: indole 0.06%, muscalure (at 50% cis-9-tricosene) 1.59%, tri-methylamine-hydrochloride 15.86%, ethyl alcohol 34.90%, and powdered sugar 47.59%. One-half gallon of formulation E finished attractant was tested in the commercially available Big Stinky Fly Trap (J.L. Price Products, South Milwaukee, Wis.) set up six feet away from another Big Stinky Fly Trap concurrently baited per label directions with fresh liver and Control Fluid, a commercial insecticide sold with and only for use in Big Stinky Fly Traps. An additional trap baited with liver and Control Fluid as above, but left to putrefy in the absence of flies for two days prior to the commencement of the test, was set six feet from the formulation E trap, opposite the fresh liver trap, and opened to fly activity at 1315 hours, concurrent to baiting of the other traps. The ratio of flies caught in the traps by 0645 hours the following morning are shown in Table III.

TABLE III

| FORMULATION | FLY COUNT (RATIO) |
|---|---|
| Fresh Liver | 1.0 |
| Putrefied Liver | 1.2 |
| E | 10.2 |

The trapping results for the synanthropic fly clearly demonstrates the superior performance provided by the present invention.

EXAMPLE IV

The ability of the present invention to exert a greater attractant effect on the female house fly is shown by tests performed with a series of traps hung serially along a fence proximate to a horse stable in Phoenix, Ariz. Two distinct types of traps and four attractant compositions were used with a duplicate of each being provided for corroboration.

The traps employed for the tests were the Fly Terminator Trap (FT), a mechanical trap which does not employ an insecticide and the Fly Stik Trap which is comprised of a vertical cylinder coated with an adhesive and having opposing end caps. Both traps are sold by the Farnam Companies, Inc. of Phoenix, Ariz. The present invention was used in dilute form with a water carrier in both FT traps used in the tests.

The six Fly Stik traps utilized were prepared in three different ways. The first pair (A) was baited with a tricosene-sugar attractant, the second pair (B) was baited with undiluted attractant prepared in accordance with the present invention and the third pair (C) was left unbaited as control. All traps were hung about 2m from the ground along an E-W with 2m spacing therebetween.

The fly attractant of the present invention was prepared by emulsifying cis-9-tricosene in a hydrochloride solution of indole and trimethylamine hydroalcoholic in the following proportions by weight: muscalure 2.21 (at 65% cis-9-tricosene or 1.44), indole 0.06%; trimethylamine-HCl 18.58; emulsifier 0.98; alcohol 76.17, water 2.0. The water accentuates dissolution of the trimethylamine-HCl while the indole serves as a feeding attractant with the alcohol serving not only as the solvent therefor, but also as the liquid carrier. The tricosene level was increased to a level twice that used in the liquid concentrate of Formulation E.

The FT traps were each baited with one fluid ounce of the attractant diluted in one-half gallon of tap water. The Fly Stik traps marked B were each baited with the undiluted attractant by placing 10 mil in the bottom cups of the traps. As mentioned, the Fly Stik traps marked C were left unbaited as controls. The remaining pair of Fly Stik traps marks A were baited with 4 g. of 0.15% cis-9-tricosene on sugar spread evenly across the adhesive surface of the traps.

The eight traps were attached to the stable eaves and left in place for twenty-two hours before removal. Sex ratios were determined from a subsample of 200 flies taken from each trap. In the case of the Fly Stik traps only house flies trapped on the adhesive surface were counted. All flies drown in the fluid at the bottom cups were not counted.

The total fly counts and sex ratios for the eight traps are shown in the following table.

TABLE IV

| POSITION | BAIT | HOUSE FLIES ||||
|---|---|---|---|---|---|
| | | MALES | FEMALES | RATIO | TOTAL |
| 1 | A | 98 | 102 | 0.96 | 391 |
| 2 | C | 101 | 99 | 1.02 | 331 |
| 3 | FT | 63 | 137 | 0.46 | 971 |
| 4 | B | 91 | 109 | 0.83 | 652 |
| 5 | A | 100 | 100 | 1.00 | 596 |
| 6 | FT | 66 | 134 | 0.49 | 1334 |
| 7 | B | 86 | 114 | 0.75 | 696 |
| 8 | C | 95 | 105 | 0.91 | 211 |
| | A | 198 | 202 | 0.98 | 897 |
| | B | 177 | 223 | 0.79 | 1348 |
| | C | 196 | 204 | 0.96 | 542 |
| | FT | 129 | 271 | 0.48 | 2305 |

As noted from the data, the FT traps baited with the present attractant diluted in water at a 1:63 ratio caught over 2.5 times as many flies as the FLY STIK traps (A) baited with the cis-9-tricosene pheromone alone. The Fly Stik traps (B) baited with the undiluted attractant of the present invention trapped about 1.5 times as many flies as those baited by the pheromone alone. Since there were a substantial number of flies drowned in the liquid of traps (B) that were not counted, the totals for traps (B) read lower than the actual performance.

The surprising aspect of the use of the attractant both in the diluted and full strength tests were the low ratios of male to female flies. In marked contrast thereto, the Fly Stik traps A and C, baited with the pheromone alone and unbaited, respectively, both showed a male:female ratio of nearly one. Thus, the present attractant exhibits an effect that is quite beneficial to one attempting to achieve a longer term reduction in the fly population since not only is the attractant successful in attracting a greatly increased number of flies, the proportion of females killed enhances the performance of the composition.

The attractant compositions of the present invention may be made in concentrated form containing ethyl alcohol to which may be added a suitable additional carrier. The use of the trimethylamine hydrochloride as the constituent to provide trimethylamine gas when exposed to moisture provides an attractant composition which has a considerably less noxious odor to humans until the dissociation in the presence of water takes place. Although the foregoing tests show the efficacy of the present invention when mixed with ethyl alcohol and sugar, it is to be noted that other carriers such as, but not limited to, corn cob, grits, water, cellulose, talc, various clays, sand and other silicates can be used singularly or in combination, if desired. The commercial ethyl alcohol product used herein typically contains 5 parts isopropanol to 100 parts ethanol (B.A.T.F. formula S.D.A.-3C). It is low in cost and, if desired, water can be added for further savings.

The attractant compositions of the present invention may be used in conjunction with traps and electrocutors, or may be used in conjunction one or more insecticides. Such insecticides include, but are not limited to: bomyl, dimethyl-3-hydroxy glutaconate dimethyl phosphate, which in Example II is provided with a chlorinated hydrocarbon in the first phase mixture to enhance the stability thereof; carbonfuran, 2, 3-dihydro-2, 2-dimethyl-7-benzofuranyl methylcarbamate; dichlorvos, 2, 2-dichlorovinyl dimethyl phosphate; iodofenphos, 0. O-dimethyl -O-(2, 5-dichloro-4-iodophenyl) phosphorthioate; methomyl S-methyl-N-((methylcarbamoyal) oxy)-thioacetimidate; and propoxur, 2-(1-methylcarbamoyl) phenyl methylcarbamate. The percentage of weight of insecticide added to the attractant composition for desirable results is determined in part by the toxicity of the insecticide selected, with the range of 0.05% to 15% by weight of the attractant composition for insecticide being found satisfactory. The higher concentrations of insecticide being required for aerosol applications of the subject invention. Additionally, dispersing agents, emulsifiers, surfactants, rheology controlling agents, such as xanthan gum as added in Example II, preservatives, conditioners, and the like may be variously employed in combination with the present invention without departing from the scope of the invention as claimed.

What is claimed is:

1. A synergistic attractant composition for synanthropic flies which comprises:
   (a) a feeding attractant selected from the group consisting of indole and skatole; said attractant being presented in a quantity within the approximate range of 0.01 to 0.10 weight percent;
   (b) cis-9-tricosene present in a quantity within the approximate range of 0.025 to 1.44 weight percent;
   (c) trimethylamine hydrochloride;
   (d) alcohol to serve as a solvent for said feeding attractant; and
   (e) a suitable carrier.

2. The composition of claim 1 wherein said trimethylamine hydrochloride is present in a quantity of at least 0.5 weight percent.

3. The composition of claim 1 wherein said alcohol is present as a solvent in a quantity of at least 0.5 weight percent.

4. The composition of claim 1 wherein said carrier includes water as a constituent.

5. The composition of claim 1 further comprising an insecticide added thereto.

6. A synergistic attractant composition for synanthropic flies which comprises:
   (a) a feeding attractant selected from the group consisting of indole and skatole; said attractant being present in a quantity of approximately 0.01 weight percent;
   (b) cis-9-tricosene present in a quantity within the approximate range of 0.025 to 0.05 weight percent;
   (c) trimethylamine hydrochloride present in a quantity of approximately 0.5 weight percent;
   (d) ethyl alcohol to serve as a solvent for said feeding attractant; and
   (e) a suitable carrier.

7. The composition of claim 6 wherein said alcohol is present as a solvent in a quantity of approximately 0.5 weight percent.

8. The composition of claim 6 wherein said carrier includes water as a constituent.

9. The composition of claim 6 further comprising an insecticide added thereto.

10. A synergistic attractant composition for synanthropic flies which comprises:
    (a) a feeding attractant selected from the group consisting of indole and skatole; said attractant being presented in a quantity within the approximate range of 0.01 to 0.10 weight percent;
    (b) cis-9-tricosene present in a quantity within the approximate range of 0.025 to 1.44 weight percent;
    (c) trimethylamine hydrochloride; and
    (d) a suitable carrier.

* * * * *